United States Patent [19]
Hein et al.

[11] Patent Number: 5,674,221
[45] Date of Patent: Oct. 7, 1997

[54] EXTERNAL FIXATOR WITH IMPROVED CLAMP AND METHODS FOR USE

[75] Inventors: Todd J. Hein, Minneapolis, Minn.; Jude L. Sasing, Manilla, Philippines

[73] Assignee: Orthopaedic Innovations, Inc., Minneapolis, Minn.

[21] Appl. No.: 546,870

[22] Filed: Oct. 23, 1995

[51] Int. Cl.⁶ .................................................. A61B 17/60
[52] U.S. Cl. ............................. 606/54; 606/59; 606/61; 606/65
[58] Field of Search ..................... 606/54, 59, 61, 606/65, 66, 67

[56] References Cited

U.S. PATENT DOCUMENTS 5,507,746  4/1996  Lin ............................................ 606/60

Primary Examiner—Michael Buiz
Assistant Examiner—Daphna Shai
Attorney, Agent, or Firm—Gregory F. Cotterell

[57] ABSTRACT

A low cost and easy to assemble external fixator for the stabilization of a bone fracture is disclosed. The assembly of the external fixator makes use of a clamp to secure a pin to a stabilization bar. The body of the clamp will have an indentation that can be placed over the stabilization bar. Each arm of the indentation will have a hole with the two holes being aligned such that a single pin can be placed through both holes across the mouth of the indentation. Once the stabilization bar is within the indentation a pin can be inserted through the two holes in the arms of the body to restrain the stabilization bar within the clamp. The clamp will have a force applicator such as a screw that will lock both the stabilization bar and pin to prevent relative motion of the stabilization bar and the pin relative to the clamp. The preferred clamp will have a retaining clasp for gripping the stabilization bar to resist the separation of the stabilization bar from the clamp.

21 Claims, 7 Drawing Sheets

EXTERNAL FIXATOR WITH IMPROVED CLAMP AND METHODS FOR USE

FIELD OF THE INVENTION

The invention relates to an external fixator for the healing of fractured bones where the external fixator has an improved clamp for positioning and fixing the pins to the stabilization bar. More specifically, the invention relates to the use of clamps that can be easily attached and disattached to the stabilization bar and that preferably are self retaining on the stabilization bar.

BACKGROUND OF THE INVENTION

External fixation provides fracture stability to a bone structure external to the patient. This procedure is less technically demanding and less invasive compared to internal fixation using plates and nails. External fixation achieves immediate stabilization of the fracture without compromising bone vascularity. Post-operative management is enhanced because the device permits access to soft tissue wounds reducing the risk of infection, and the external fixator can be more easily adjusted to enhance fracture healing. To stabilize the bone, pins can be placed into the bone protruding out from the skin of the patient on both sides of the fracture. These pins are then attached to some form of stabilization bar that holds the pins firmly with respect to each other.

Typically, a plurality of pins are used on each side of the fracture. At least two pins with one on each side of the fracture are used, but preferably four or more pins total are often used. The support provided by the stabilization bar is conveyed by the pins to the bones surrounding the fracture. An x-ray is used to examine the characteristics of the fracture.

Optimum pin placement is a function of the anatomical and biomechanical requirements to stabilize the individual fracture. For example, transverse non-displaced fractures, pin placement is easily aligned with the side or stabilization bar. For fractures involving displaced and comminuted bone, optimum pin placement requires more adjustability of the pin clamp and/or stabilization bar. For most fractures, the range of placement required for pin position is limited to longitudinal displacement and minimal transverse angulation relative to a fixed orientation.

While fractures can take many forms, about seventy percent of all fractures are straight line fractures passing generally from one side of the bone to the other across the diameter of the bone. For straight line fractures, the pin placement will usually be protruding essentially radially from the bone. The remaining approximately thirty percent of fractures are predominantly along the length of the bone. To stabilize these longitudinal fractures it may be necessary to place pins at an angle relative to the radial direction from the bone. As a result, a portion of these thirty percent of fractures may require a clamp with the added flexibility needed for attachment to the stabilization bar to accommodate the pins at an angle relative to the radius of the bone. Looked at from the other perspective, the placement of an external fixator for most fractures does not require a clamp that can attach to pins placed at an angle relative to the radial direction relative to the bone.

Commercially available external fixators come in several different variations. Current external fixator designs accommodate optimum pin placements by combining range of motion of the pin clamp and frame adjustability. Individual pin clamps designed to accommodate a single pin provide an optimum range of positioning. A commonly used system has clamps that slide over the stabilization bar and pivot both around the bar and around an axis radially projecting from the bar. The drawback of this design is that in a majority of fractures it may provide unnecessary ranges of motion making the clamp more complex and costly than necessary. Two screws are needed to tighten the clamp on the stabilization bar and the pin within the clamp.

Furthermore, during the treatment of the injured patient, it may be useful to change the number of pins, either to increase the number to have more stability due to further injury or improper healing or decrease the number, for example as healing has progressed. With the type of clamps previously available, significant effort is needed to change the number of pins being accommodated because the clamps must be slid onto the bar from the end of the stabilization bar.

Other designs have more elaborate relationships between the bar and the clamp where the clamp essentially becomes an integral part of the bar itself and/or where the clamp can accommodate more than one pin. These more elaborate designs have increased costs and various restraints on the placement of the pins.

There is currently pressure to reduce medical expenses. As a result there is demand for less expensive medical products and for products that reduce the time devoted by health professionals in their use. Existing external fixators have not been well designed from the perspective of reducing medical expenses.

SUMMARY OF THE INVENTION

The invention provides a low cost and easy to use external fixator. The assembly of the external fixator makes use of a specially designed clamp to secure a pin to a stabilization bar. A plurality of pins may be used with one clamp for each pin. The pins are placed in appropriate locations to stabilize the bone fracture. The pins are placed into the bone radiating approximately from a common axis in order for their attachment to a single stabilization bar. A plurality of stabilization bars can be combined to form structures capable of providing greater stabilization for some fractures and appropriate stabilization for a greater variety of fractures.

The body of the clamp will have an indentation that can be placed over the stabilization bar. The indentation will be preferably generally U-shaped. Each arm on the sides of the indentation will have a hole or slot with the two holes being aligned such that a single pin can be placed through both holes across the mouth of the indentation. In this way, the clamp can be placed over the stabilization bar at any position of the bar without needing to slide the clamp from an end of the stabilization bar.

Once the stabilization bar is within the indentation, the pin can be inserted through the two holes in the arms of the body to restrain the stabilization bar within the clamp. The clamp will also have a force applicator for applying a force to the stabilization bar pushing it against the pin. The actuation of the force applicator will lock both the stabilization bar and the pin to prevent their sliding and therefore to stop any motion relative to the clamp.

The preferred external fixator will have a clamp that has a retaining clasp for gripping the stabilization bar to resist the separation of the stabilization bar and the clamp even when the pin is not in place. The preferred retaining clasp will have two opposing surfaces where at least one of the surfaces can flex in response to the force of the stabilization bar being inserted within the U-shaped indentation. A particularly convenient retaining clasp has a U-shaped member that is attached to the clamp at the rear portion of the "U" along the top surface. Preferably the U-shaped member is made from metal and is machined to be an integral unit with the body of the clamp. The clamp can have a second retaining clasp which may be attached to the bottom surface of the clamp. The opposing surfaces of the retaining clasp can have contours for better gripping of the stabilization bar.

The force applicator preferably includes a screw that is mated with a threaded hole in the side of the U-shaped indentation. The threaded hole is preferably at an angle approximately between 30 degrees and 60 degrees and more preferably at an angle of about 45 degrees relative to the plane generally bisecting the indentation. Alternatively, the force applicator can include a lever engaging a cam or a spring activated plunger.

To assemble the external fixator, the indentation of the clamp is engaged with the stabilization bar at the desired location of the stabilization bar based on the selected locations of the pins. A pin is then inserted through the holes in the arms of the clamp. With the pin in place, the force activator is operated to immobilize the pin and stabilization bar relative to the clamp. Prior to the insertion of the pin, the holes in the arms of the clamp, when the clamp is engaged with the stabilization bar, can be used as a guide for drilling the holes for the insertion of the pin. The self retaining property of the preferred clamp engaged with the stabilization bar is particularly useful when the clamp is used as a drilling guide.

DETAILED DESCRIPTION OF THE INVENTION

The goal of the present invention is to provide a practical, less expensive clamping system for securing the pins within an external fixator while providing an adequate clinical range of placement for the pins. At the same time the clamping system is easier to use and provides for easier modification of the configuration of the pins after placement. The clamps used in the clamping system are designed to minimize the number of parts and to have the clamp fit over the stabilization bar without needing to slide the clamp along the bar from the end of the bar. For fractures requiring oblique pin placement, this clamp can be combined with other components to expand possible pin placement. For most uses, the external fixator within the invention is suitable for the desired placement of the pins.

Figure 1:
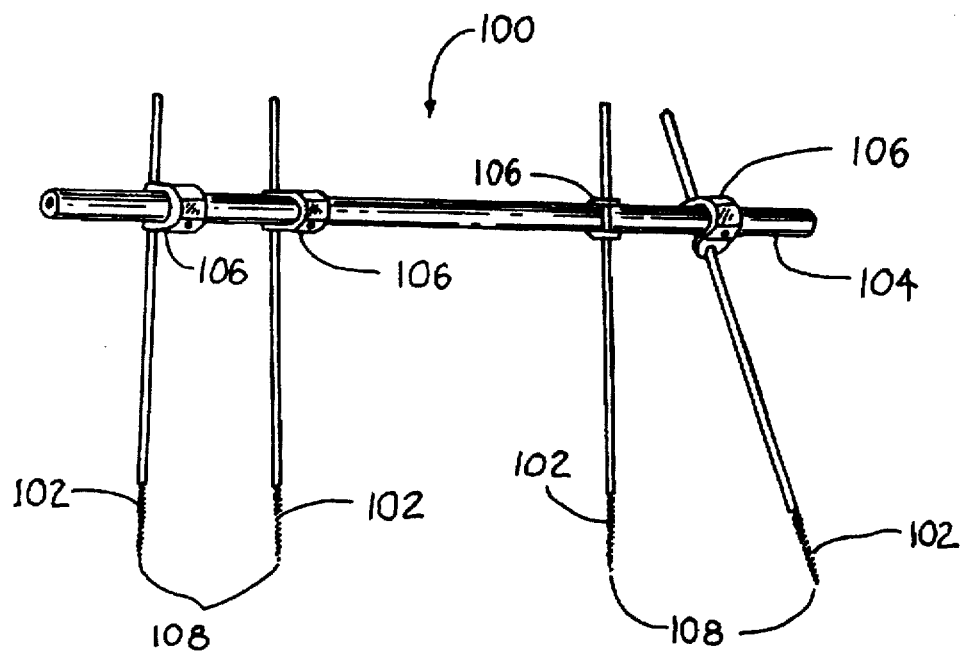
FIG. 1 is a perspective view of an external fixator of the invention assembled externally of the patient.

The basic external fixation system 100 within the invention is shown in FIG. 1. The external fixation system 100 has one or more pins 102, a stabilization bar 104 and clamps 106 for fastening the pins 102 to the stabilization bar 104. The pins 102 are conventional pins for this purpose. While the shape of the pin is not important, the pins 102 are generally long and thin with a cylindrical shape. The tip 108 will typically be pointed, although the exact shape of the tip is not important. The pins 102 should be constructed from appropriate material for temporary placement within the body. The pins 102 should be relatively rigid.

The size of the pins 102 will usually vary depending on the bone to be stabilized and on the size of the patient. It may be possible to use different size pins with a single clamp. Alternatively, different size clamps can be used with different sized pins.

The stabilization bar 104 will typically be long, relatively thin and generally cylindrical in shape. The stabilization bar 104 can have different shapes. The size of the stabilization bar 104 will depend on the desired configuration of the external fixator to be assembled. The stabilization bar 104 will generally be longer than the pins 102 and will typically have a larger diameter. The stabilization bar 104 should be rigid. The stabilization bar 104 can be made from a larger variety of materials because it does not have to be compatible with placement in the body. Appropriate materials for producing the stabilization bar 104 include a variety of metals, graphite or composites. Graphite and certain composites are advantageous because they are effectively transparent to x-rays, but metals have the advantage with respect to cost. The stabilization bar 104 may or may not be hollow.

Figure 2A:
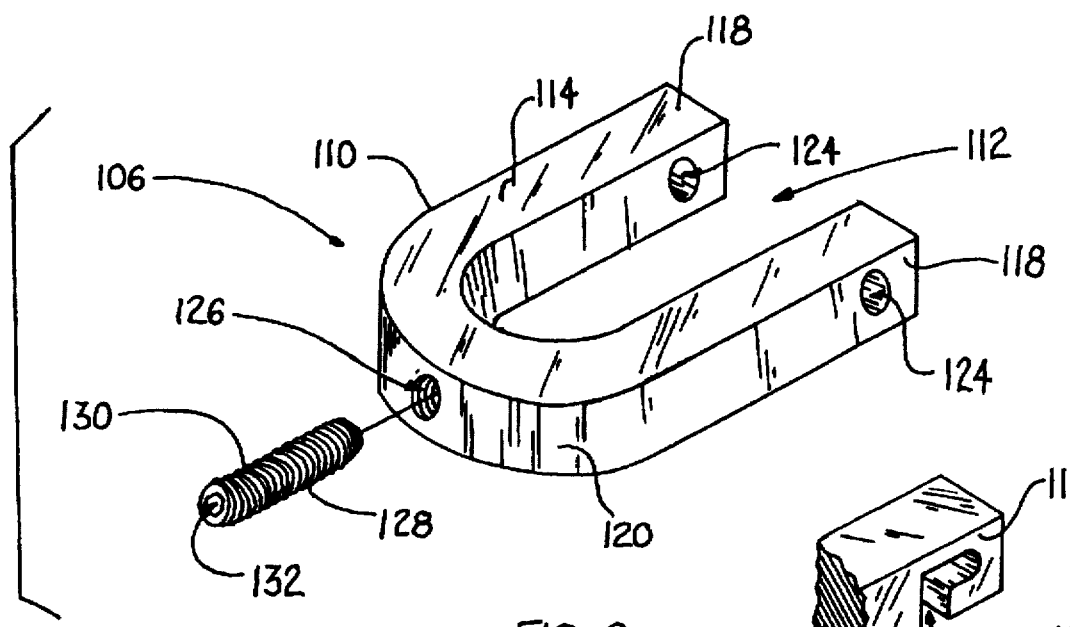
FIG. 2a is a perspective view of a clamp for attaching a pin to a stabilization bar in the construction of the external fixator where a screw is depicted separate from the threaded hole for the screw.

The clamp 106 is an important element in terms of connecting the pins 102 to the stabilization bar 104. While specific embodiments of the clamp 106 can incorporate a variety of characteristics, there are certain unifying features of the clamps 106 within the invention. Referring to FIG. 2a, the clamp 106 will have a body 110 with a indentation 112 relative to the top surface 114 and the bottom surface of the body for receiving the stabilization bar 104 when the bar 104 is oriented perpendicular to the top surface 114. The preferred indentation will be U-shaped, although other more elaborate shapes such as Z-shape can be used. The indentation 112 extends from the top surface 114 to the bottom surface of the body 110.

Figure 3:
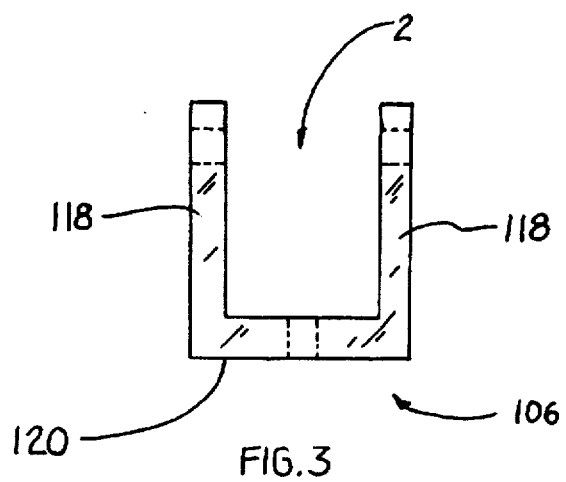
FIG. 3 is top view of a clamp of the invention with a flat connecting portion in its body joining the two arms where the edges of holes within the body of the clamp are shown in phantom lines.

The indentation 112 forms two arms 118 with one arm 118 on each side of the indentation 112 with a connecting portion 120 joining the two arms 118. The connecting portion 120 is preferably curved, and even more preferably the connecting portion is roughly semi-circular. A clamp 106 with a flat connecting portion 120 is displayed in FIG. 3.

Again referring to FIG. 2a, the surfaces along the indentation 112 form two opposing surfaces 122 along each arm 118 that are generally parallel to each other. The diameter of the connecting portion 120 (or length if it is flat) should preferably be approximately the diameter of the stabilization bar 104 or larger. Therefore, the stabilization bar 104 should be able to fit between the arms 118 of the indentation 112 to rest against the connecting portion 120 of the indentation 112. In some embodiments, other structure will support the stabilization bar 104 within the indentation 112 such that it may not contact the connecting portion 120. A single clamp 106 may be used with different diameter stabilization bars 104.

Figure 2B:
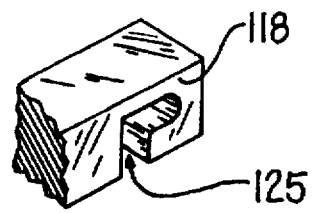
FIG. 2b is a cut away perspective view of the body of the clamp with a lot in an arm.
Figure 2:
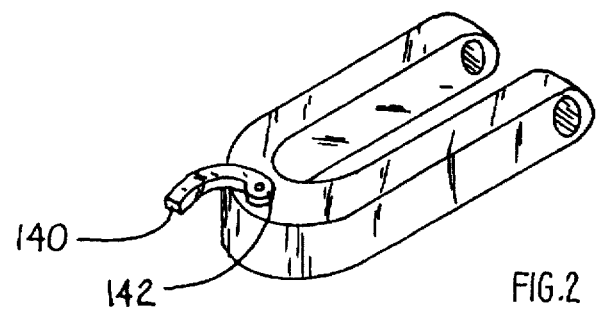
FIG. 2c is a perspective view of a clamp having a lever and cam acting as a force applicator.

Each arm 118 has a hole 124 along the side of the clamp 106 going from the outer edge to the inner, opposing surfaces 122. The hole can have a slot leading from it as shown in FIG. 2b to permit sliding the pin into the holes. The term hole will be used to indicate either a hole with or without a slot. The holes 124 through the arms 118 are aligned such that a single pin 102 will pass through both holes 124. The diameter of the holes 124 will preferably be approximately the diameter of the pin 102 or larger. The holes 124 will be positioned along the arms 118 such that the pin 102 will almost contact the stabilization bar 104 when the stabilization bar 104 is in place within the indentation 112 and the pin 102 is within the holes 124. A single clamp 106 may be used with different diameter pins 102.

A third hole 126 can also be used along the side of the clamp 106 from the outer edge to the inner surface of the U-shaped indentation 112. The third hole 126 can be used to accommodate a force applicator. The preferred force applicator will include a screw 128. When the force applicator includes a screw, the third hole 126 will preferably have threads for receiving the screw 128. The screw 128 will have threads mated to the threads of the third hole 126. The head 130 of the screw 128 can have a variety of shapes. A convenient form of the head 130 would have a hexagonal hole 132 for receiving an allen wrench. The head 130 can be adapted such that other wrenches or drivers can be used to turn the screw.

Alternatively, to take the place of the screw, the force applicator can include a lever and cam system, a lever and spring loaded plunger or some other comparable mechanical system. These alternative systems may not require a third hole 126. Referring to FIG. 2c, a lever 140 is attached to an asymmetric cam 142. Movement of the lever 140 brings the elongated portion of the cam 142 into contact with the stabilization bar 104 to apply the retaining force. Multiple force applicators can be used.

The third hole 126 (or other appropriate force applicator) can be positioned in a variety of locations as long as the screw 128 can be placed in contact with the stabilization bar 104 when the stabilization bar 104 is within indentation 112. When the screw 128 is screwed against the stabilization bar 104, the clamp 106, pin 102 and stabilization bar 104 are all locked in relative position. The third hole 126 can be placed, for example, at the middle of the connecting portion 120, as shown in FIG. 2a.

Figure 4:
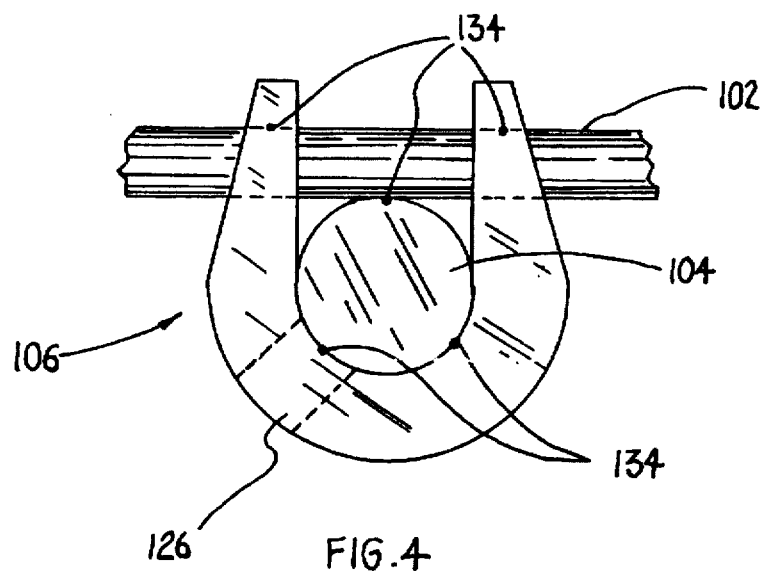
FIG. 4 is a top view of a clamp where the screw hole is placed at an angle relative to the plane bisecting a U-shaped indentation to generate three points of contact for the stabilization bar and the pin with the edges of holes through the body of the clamp depicted in phantom lines.

Referring to FIG. 4, the preferred location of the third hole 126 is rotated relative to a plane bisecting the middle of the connecting portion 120 around the axis of the stabilization bar 104 when the stabilization bar 104 is contacting the connecting portion 120. With the third hole 126 in this preferred location, the bar and pin will each be held in place at effectively three contact points 134, as depicted in FIG. 4. Having three contact points 134 guarantees that any torque will be countered by, at least, two non-collinear forces. It is more preferred to have the third hole 126 at approximately 45 degrees relative to the plane bisecting the indentation 112. The clamp may have some asymmetries, but the more preferred location of the hole 126 will be determinable from the point of contact with the stabilization bar 104 to have the three contact points roughly equally spaced around the stabilization bar 104.

The screw 128 can have any reasonable length, but it will preferably have a relatively short length such that it does not protrude from the third hole 126 when it is contacting the stabilization bar 104. If the screw 128 protrudes from the third hole 126, it would provide an unwanted projection from the clamp 106. One advantage of using a longer screw is the option of using a thumb screw head that removes the need for a tool to rotate the screw. The clamp 106 can be made from a variety of rigid materials, but metals are particularly convenient from a cost and machining point of view.

Figure 5A:
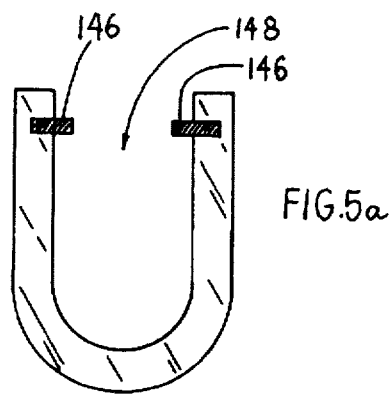
FIG. 5a is a top view of a clamp with elastic knobs to provide the self retention property of the clamp.

Preferred embodiments of the clamp will be self retaining when engaged with the bar 104. There are various ways of making the clamp self retaining. For example, a more elaborate shape of the indentation may provide some self retaining properties. FIGS. 5 and 6 depict clamps where the arms of the clamp flex to provide the self retaining property. FIG. 5a depicts an embodiment where the self retaining property is provided by elastic knobs 146 protruding into the indentation 148. The elastic knobs 146 are preferably made from rubber or other rubber-like polymer.

Figure 5B:
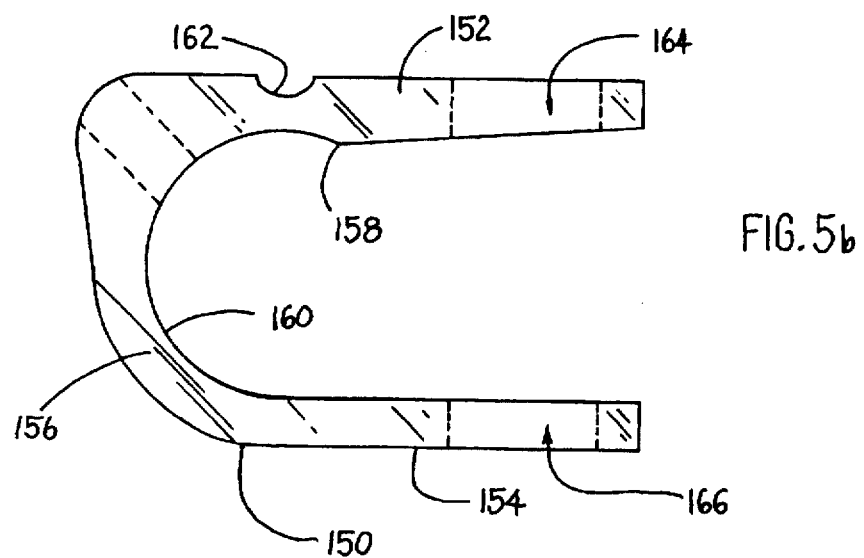
FIG. 5b is a top view of a clamp where one arm flexes relative to the opposing arm to provide a self retaining property of the clamp on a stabilization bar where edges of holes through the body of the clamp are shown in phantom lines.
Figure 6:
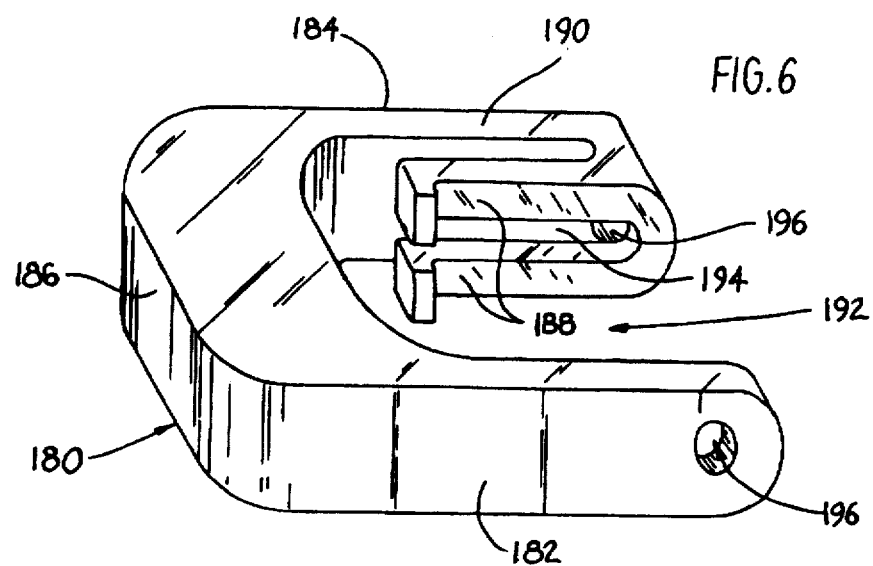
FIG. 6 is a perspective view of another embodiment of a clamp where one arm flexes relative to the opposing arm to form a retaining clasp.

Referring to FIG. 5b, the clamp 150 has asymmetric arms 152, 154. The arms 152, 154 are connected by a curved connecting portion 156. The curve of the connecting portion 156 extends beyond the end of the curved section on opposite side of the clamp 150 to from a ridge 158 where the connecting portion meets arm 152.

The closest distance from the ridge 158 to the opposite arm 154 will preferably be slightly less than the diameter of stabilization bar 104. Therefore, the arms 152, 154 must flex relative to each other for the stabilization bar 104 to contact the inner surface 160 of the connecting portion 156. A notch 162 in arm 152 provides relief for the arm 152 so that it can flex relatively elastically. In summary, the clamp 150 will snap onto the stabilization bar 104 and will stay in place due to the contact of ridge 158 with the stabilization bar 104. The arms 152, 154 will have aligned holes 164, 166 for the insertion of a pin 102.

An alternative design where the arms of the clamp assist with the self retention of the clamp on the stabilization bar 104 is depicted in FIG. 6. The clamp 180 has asymmetric arms 182, 184 joined by connecting portion 186. Arm 184 has two spring sections 188 that flex relative to the rigid section 190 of arm 184. The distance from spring sections 188 of arm 184 to the opposite arm 182 should be slightly less than the diameter of the stabilization bar 104. Therefore, when the stabilization bar 104 is placed within the indentation 192, the stabilization bar 104 is gripped between arm 182 and spring sections 188. In this embodiment, the stabilization bar 104 will not necessarily contact the connecting portion 186. The separation 194 between spring sections 188 is located such that a pin 102 passing through aligned holes 196 passes through separation 194.

A variety of other designs where flexing of one or both arms (symmetric or asymmetric) provides the self retention property can be used. Similarly, grooves in the wall of the indentation can support a coil spring, leaf spring or comparable structure or structures to provide the self retaining property.

Figure 7:
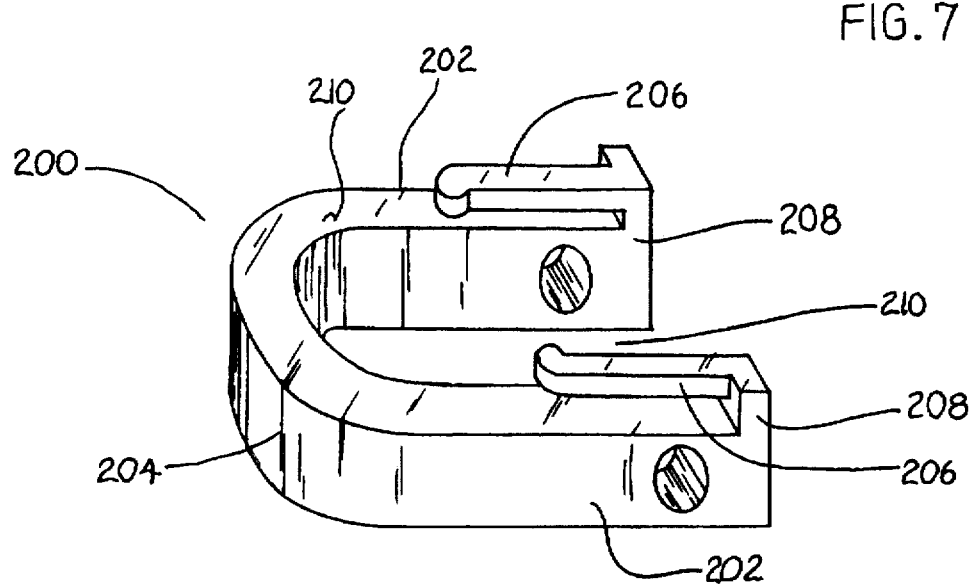
FIG. 7 is a perspective view of a clamp with a retaining clasp attached to a surface of the clamp near the front of the U-shaped indentation.
Figure 8:
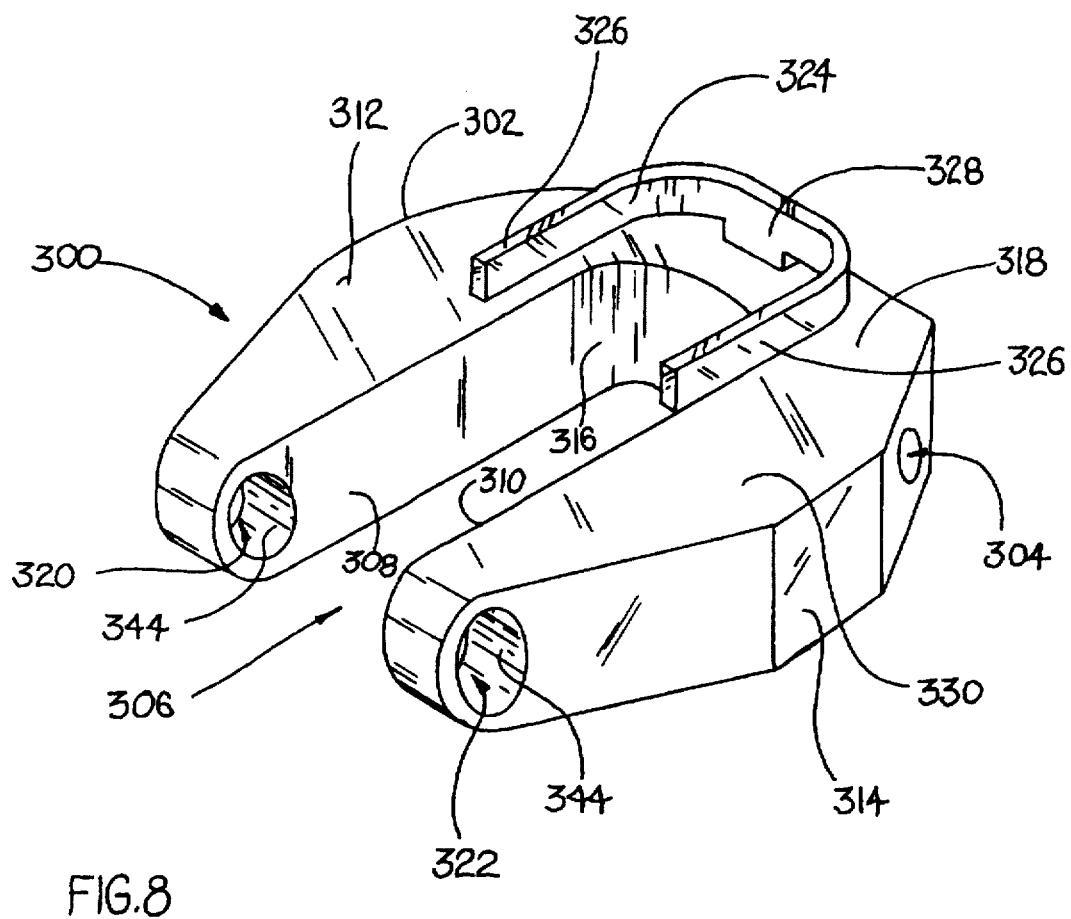
FIG. 8 is a perspective view of another embodiment of a clamp with a retaining clasp attached to a surface of the clamp where the retaining clasp is attached along the connecting portion joining the two arms.

The self retaining character of the clamp does not have to be provided by the arms of the clamp. For example, referring to FIG. 7, the clamp 200 has roughly symmetric arms 202 joined by a curved connecting portion 204. Flexible appendages 206 are attached to each arm 202. The two flexible appendages 206 are mirror images of each other. Each flexible appendage 206 is connected to its respective arm 202 by a support 208. The supports 208 projects upward from the top surface 210 of clamp 200. In a preferred construction of clamp 200, the arms 202, the supports 208 and the corresponding flexible appendages 206 form an integral unit machined from a single piece. Alternatively, the flexible appendages 206 can be reversibly attachable and detachable from the corresponding arm 202 with corresponding straightforward modifications to the support 208.

Due to their elastic properties, the flexible appendages 206 act as springs. The distance between the two flexible appendages 206 should be slightly less than the diameter of the stabilization bar 104. When the stabilization bar 104 is placed lengthwise into the indentation 210, the flexible appendages 206 grip the stabilization bar 104 to provide the self retaining properly of the clamp 200. When gripped by the flexible appendages 206, the stabilization bar 104 does not necessarily contact the connecting portion 204. A second pair of flexible appendages can be attached at the bottom surface of clamp 200 in an equivalent way as the flexible appendages 206 are attached to the top surface 210. Using two pairs of flexible appendages provides somewhat greater retaining property in exchange for the additional machining required.

FIGS. 8–11 depict a particular preferred embodiment of the clamp. In this embodiment, the body 302 of clamp 300 is slightly asymmetric to provide a slightly longer screw hole 304. The precise shape of the body is not significant, and the screw hole 304 can be made shorter if desired. A U-shaped indentation 306 is bounded by two flat portions 308, 310 along the inner surface of arms 312, 314 respectively. The flat portions 308, 310 can have surface roughness to enhance the friction provided by the surfaces. The flat portions 308, 310 are joined by a semicircular surface 316 along the inner surface of connecting portion 318. Aligned pin holes 320, 322 penetrate arms 312, 314 respectively through flat surfaces 308, 310.

Figure 9:
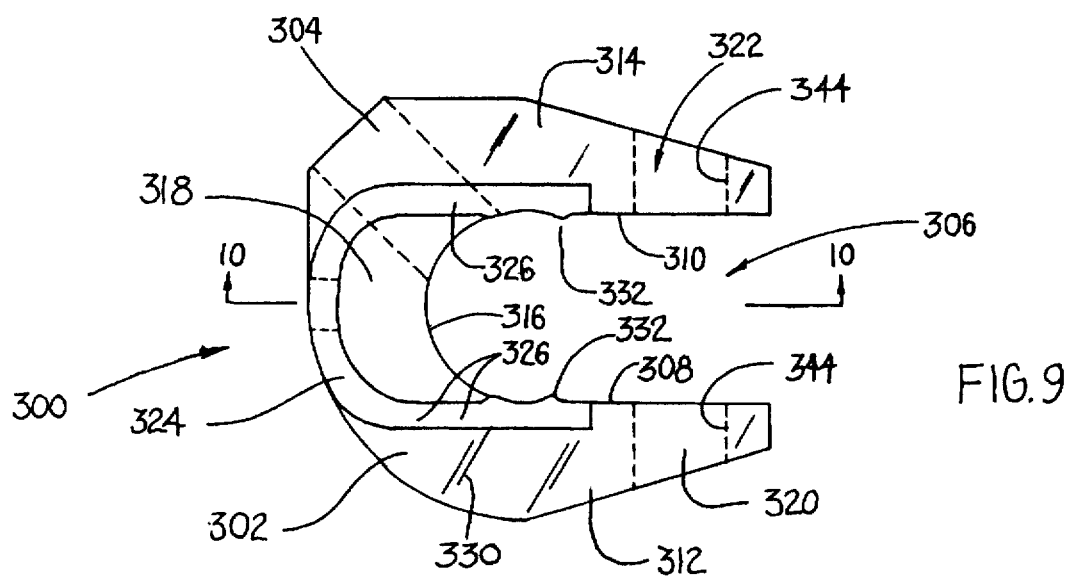
FIG. 9 is a top view of the clamp depicted in FIG. 8 with the edges of holes through the body of the clamp and structure under the retaining clasp depicted with phantom lines.
Figure 10:
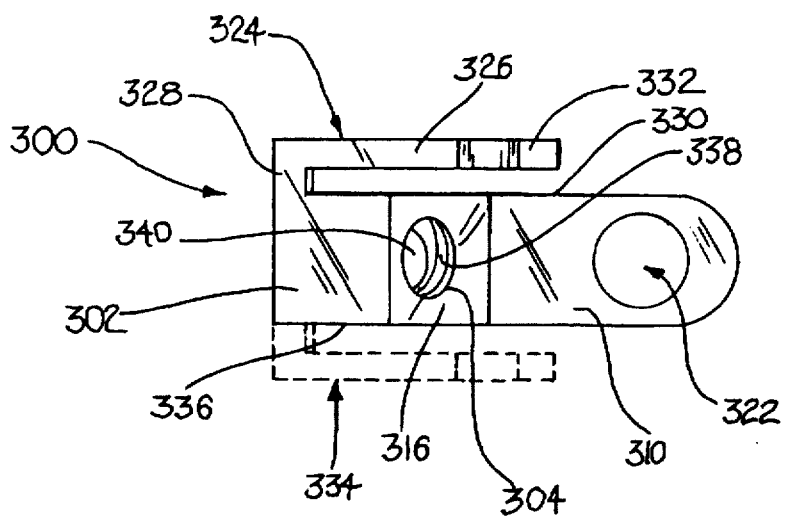
FIG. 10 is a sectional view of the clamp of FIG. 9 taken along line 10—10 where a second retaining clasp is shown in phantom lines attached to the lower surface of the clamp.
Figure 11:
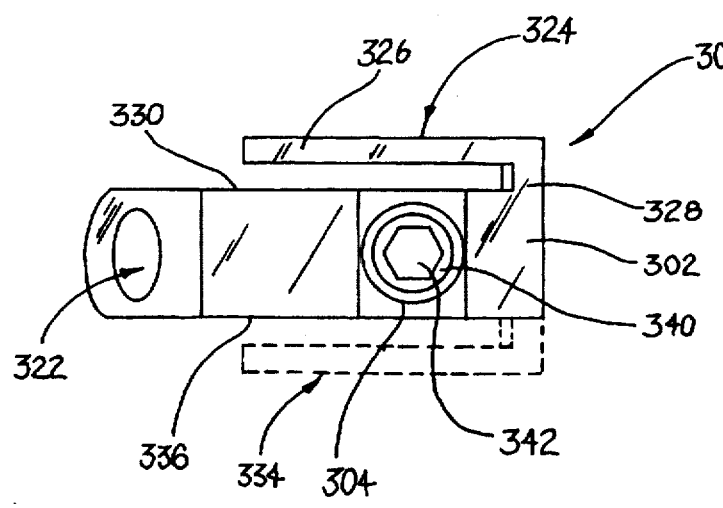
FIG. 11 is a side view of the clamp of FIG. 8 looking along the screw hole.

Spring clasp 324 is preferably U-shaped although other shapes can be used if they provide matched prongs 326. Spring clasp 324 is attached to the body 302 by support 328. Support 328 preferably attaches to the rear part of connecting portion 318 along top surface 330 although it can be attached at other locations along the connecting portion 318. Referring to FIGS. 9 and 10, the opposing inner faces of prongs 326 preferably have bumps or contours 332 corresponding to the radius of the stabilization bar 104. The distances between the peaks of the bumps 332 of the opposing inner faces of prongs 326 should be slightly greater than the diameter of the stabilizing bar 104. The distance between the opposing flat portions 308, 310 is approximately equal or less than the diameter of the stabilizing bar 104. When the clamp 300 is engaged with the stabilizing bar 104, bumps 332 assist with gripping the stabilizing bar 104 and, thereby, providing the self retaining property of the clamp 300.

The spring clasp 324 and the body 302 of clam 300 are preferably machined from a single piece of metal. Alternatively, the spring clamp can be machined from a separate piece of material and either permanently attached to body 302 by welding or the like or reversibly removable from the body 302 by some appropriate engagement mechanism. For greater self-retaining properties of the clamp, a second spring clasp 334 can be optionally attached to the bottom surface 336 of clamp 300, as shown with phantom lines in FIGS. 10 and 11.

The plane bisecting the screw hole 304 perpendicular to top surface 330 passes through the center of the circle defining the semicircular surface 316. This plane bisecting the screw hole is preferably at a 45 degree angle to the plane bisecting flat portions 308, 310. Screw hole 304 preferably has threads 338. Screw 340 engages threads 338. Screw 340 can have a hexagonal hole 342 for engagement with an allen wrench, or it can have slots for engaging a screw driver, or it can be designed to engage some other type of driver or wrench.

If a stabilization bar 104 is placed within U-shaped indentation 306 and a pin 102 is inserted through holes 320, 322, driving the screw 340 inward will apply a force that tightens stabilization bar 104 against screw 340, pin 102 and curved surface 316 and that tightens pin 102 against stabilization bar 104 and surfaces 344 inside hole 320, 322. The forces are roughly as depicted in FIG. 4. Screw 340 can be replaced with a lever and cam or comparable mechanism for applying force to the stabilizing bar 104 engaged within U-shaped indentation 306.

Figure 12:
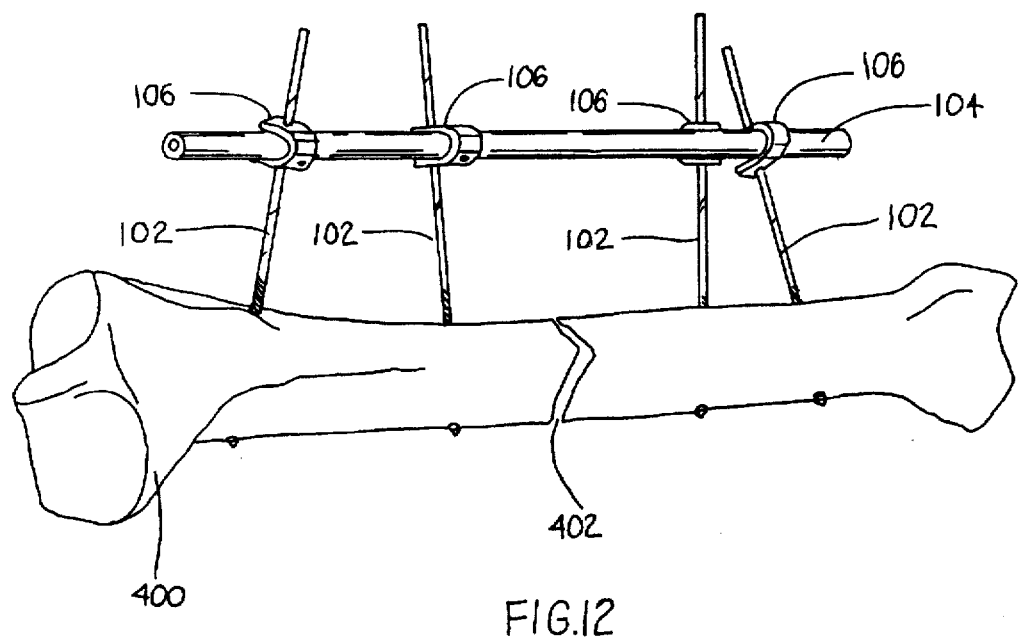
FIG. 12 is a perspective view of an external fixator of the invention depicted connected to a bone to stabilize a fracture with tissue surrounding the bone and adjacent bones removed for simplified viewing.
Figure 13:
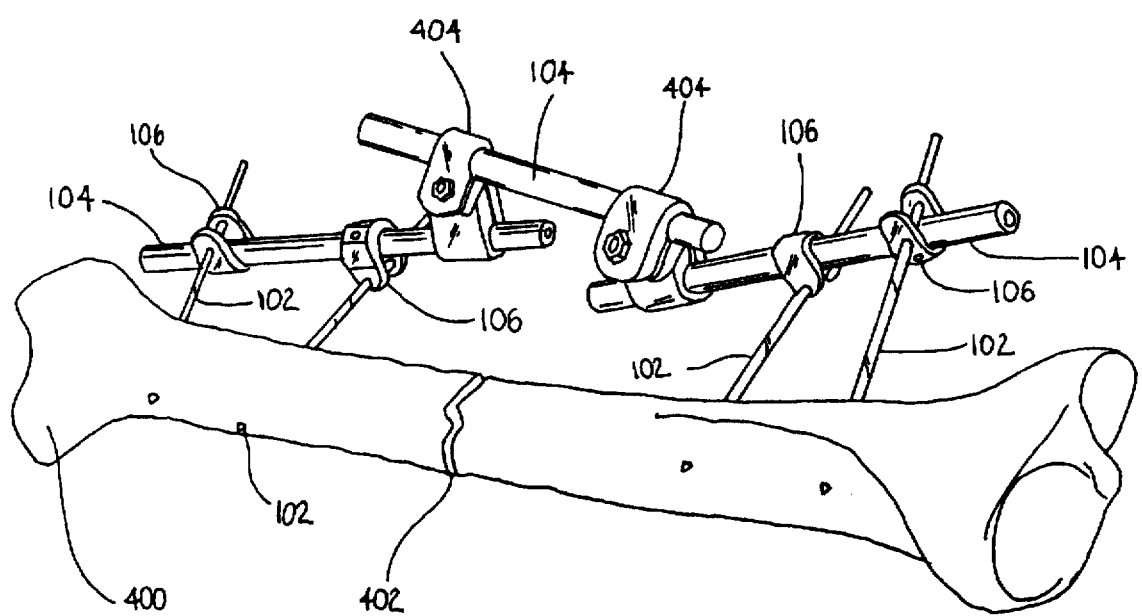
FIG. 13 is an alternative arrangement of the external fixator to stabilize a similar fracture as depicted in FIG. 12 where multiple stabilization bars are used.

Clamps within the invention do not provide for the rotation of the pin 102 relative to the longitudinal axis of the stabilization bar 104. Nevertheless, the clamps provides considerable flexibility for the construction of external fixation frameworks. As shown in FIG. 12, the clamps 106 rotate around the stabilization bar 104 (when the screw is not tightened down) for attachment to pins 102 radially protruding from the bone 400 at different angles. In FIG. 12, there are two pins on each side of fracture 402. Referring to FIG. 13, clamps 106 can be oriented on opposite sides of stabilization bar 104. Greater flexibility can be obtained by using a plurality of stabilizer bars 104. In FIG. 13, a stabilizing bar 104 is used for each side of fracture 402 of bone 400. The two stabilizing bars 104 are joined using a third stabilizing bar 104 and bar clamps 404. Other mechanisms can be used to connect the two stabilizing bars 104 on either side of the fracture 402.

Figure 14:
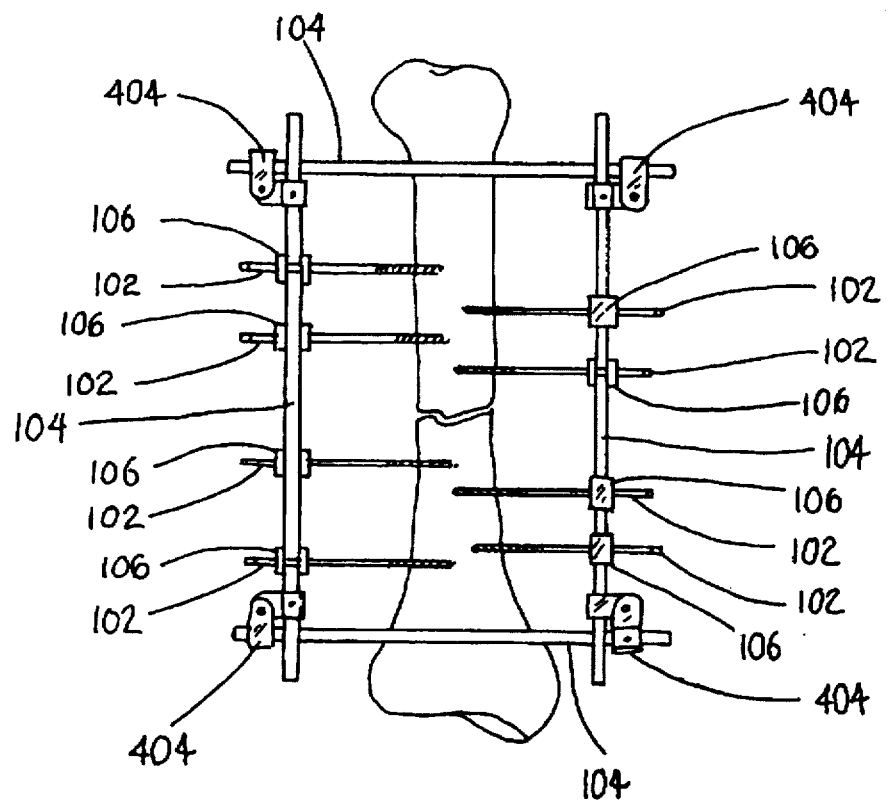
FIG. 14 is a tibial delta frame assembled using an external fixator of the invention.
Figure 15:
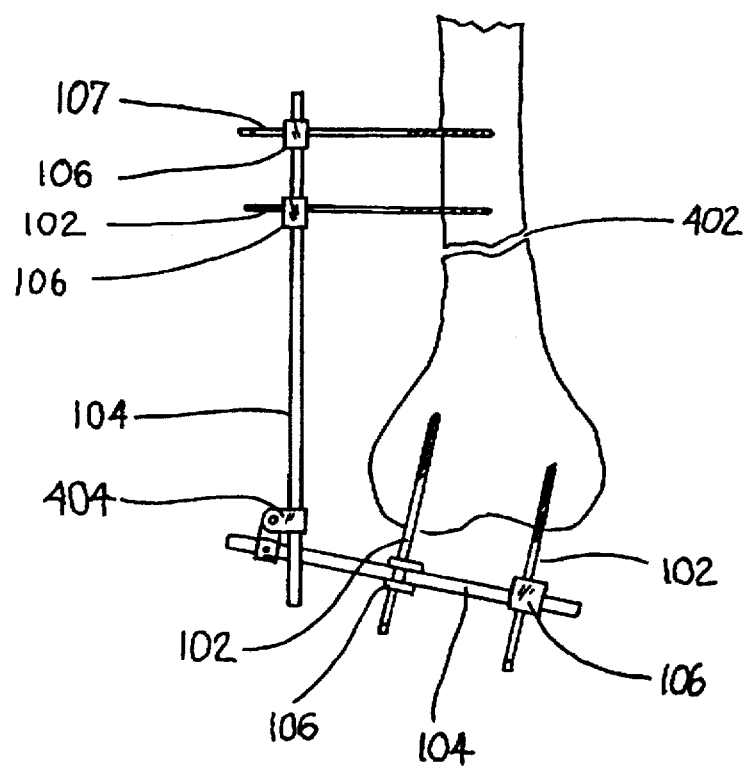
FIG. 15 is a tibial metaphyseal frame constructed using an external fixator within the invention for stabilizing a fracture near the end of the tibia.

Using multiple stabilizing bars 104, a variety of structures can be constructed either to provide greater support or to provide an appropriate structure for the particular bone and/or fracture. For example, a tibial delta frame is depicted in FIG. 14, and a tibial metaphyseal frame is depicted in FIG. 15. Therefore, even though the clamp 106 has some limits on its motion relative to the stabilization bar, a large variety of structures of external fixators can still be constructed to accommodate a large variety of fractures.

Usually, the first step in the assembly of the external fixator is the identification of the desired locations of the pins to provide appropriate stabilization of the fracture. Appropriate size pins are selected for the bone fracture to be treated. For example, bones in a hand would typically require smaller pins than would be used in an external fixator for stabilizing a fracture of the tibia in a leg. Appropriate stabilization bars would also be selected.

One clamp would then be used to fasten each pin to a stabilization bar. If a self retaining clamp is used, the clamps can first be place at the selected locations along the stabilization bars. The holes for the pins can be pre-drilled or they can be drilled using the clamps themselves at their proper locations on the stabilization bars as drilling guides. The pins are inserted into the bone using the holes drilled for the purpose. The pins are inserted through the holes in the arms of the clamp once the clamps are placed over the stabilization bar.

The force applicator is employed to lock the pin and stabilization bar relative to the clamp. Before the employment of the force applicator, many of the steps can be performed in a variety of orders based on the judgment of the physician. Use of the force applicators on all the clamps effectively completes the assembly of the external fixator to provide stabilization of the bone fracture. If there are multiple stabilization bars, these will be joined to each other using bar clamps.

A variety of specific embodiments are describe. These are not intended to be limiting.

We claim:

1. An external fixator for stabilizing a bone fracture, the external fixator comprising:
   a pin having a threaded end suitable for insertion into a bone fragment, an opposite end suitably keyed for receiving a tool for driving the pin threading into the bone fragment, and a shaft between the threaded and keyed ends having a smooth surface;
   a stabilization bar; and
   a clamp suitable for releasably securing the pin in operable engagement with the stabilization bar, wherein the clamp comprises:
      a body having two arms and an indentation therebetween with a hole through each arm, the holes having smooth bores and generally aligned with each other and suitable for receiving the pin shaft in slidable engagement through both holes simultaneously across a mouth of the indentation, the indentation suitable for slidably receiving the stabilization bar, the indentation being sufficiently deep so that the pin can be inserted through the holes in the arms when the stabilization bar is within the indentation, and a third hole having an axis at an angle to the axis of the generally aligned arm holes; and
      a force applicator, suitably engageable with and along the third hole, capable for generally applying force on said stabilization bar when within the indentation that is directed at least partially toward the pin when placed within the holes in the arms and for causing the stabilization bar to apply force on the pin such that the applied force locks the pin and the stabilization bar to resist any motion relative to the clamp.

2. The external fixator of claim 1, further comprising a retaining clasp attached to a first surface of the clamp.

3. The external fixator of claim 2, wherein the retaining clasp includes two opposing surfaces oriented along the indentation where at least one of the opposing surface can flex in response to the stabilization bar being inserted into the indentation.

4. The external fixator of claim 3, wherein the opposing surfaces are portions of a U-shaped member attached along a top surface of a connecting portion of the body between the two arms of the clamp.

5. The external fixator of claim 4, wherein the retaining clasp is made of metal and is machined to be an integral unit with the body of the clamp.

6. The external fixator of claim 4, further comprising a second retaining clasp attached to a second surface of the clamp.

7. The external fixator of claim 3, wherein the opposing surfaces include contours reciprocal to the stabilization bar surface for better gripping of the stabilization bar.

8. The external fixator of claim 1, wherein the third hole is threaded and the force applicator includes a screw that is mated with the threaded hole such that the appropriate forces are applied to the stabilization bar within the indentation when the screw is driven inward.

9. The external fixator of claim 8, wherein the threaded hole is at an angle relative to the plane generally bisecting the indentation such that force from the employment of the screw results in three points of contact for the stabilization bar and the pin.

10. The external fixator of claim 9, wherein the treaded hole is at approximately a 45 degree angle relative to the plane generally bisecting the opening of the indentation.

11. The external fixator of claim 1, wherein the force applicator includes a lever operably engaging a cam.

12. The external fixator of claim 1 wherein the two arms include slots communicating with each hole suitable for slipping the pin shaft through to the holes.

13. A clamp for securing a bone fixation pin in releasable engagement with a stabilization bar to construct at least a portion of an external bone fixator, the clamp comprising:
   a body having a connecting portion between two arms defining an indentation therebetween with a bole through each arm, the two arm holes being generally aligned with each other and having a smooth surface suitable for receiving the pin in slidable engagement through both holes simultaneously across a mouth of the indentation generally opposite from the connecting portion, the indentation having a bottom portion surface proximate the connecting portion suitable for slidably receiving the stabilization bar, the bottom portion of the indentation being sufficiently deep so that the pin can be inserted through the holes in the arms when the stabilization bar is within the indentation; and
   a force applicator, attached to the connecting portion and operably engageable between the connecting portion and the stabilization bar, capable for generally applying force directly on a portion of said stabilization bar proximate the bottom portion surface of the indentation when within the indentation and that is directed at least partially toward the pin through the stabilization bar when the pin is received within the holes in the arms and for causing the stabilization bar to apply force on the pin such that the applied force locks the pin and the stabilization bar to resist any motion relative to the clamp.

14. The clamp of claim 13, wherein the clamp further comprises a retaining clasp suitable for frictionally gripping the stabilization bar within the indentation so as to resist the separation of the clamp from the stabilization bar.

15. The clamp of claim 14, wherein the retaining clasp is a U-shaped member attached to the connecting portion of the clamp along a top surface with opposing surfaces of the arms of the U-shaped member aligned along the length of the indentation.

16. The clamp of claim 13, wherein the third hole is threaded and the force applicator includes a screw engaging the threaded hole with the threaded hole oriented at an angle relative to the plane generally bisecting the indentation such that force from the employment of the force actuator results in three points of contact for the stabilization bar and the pin.

17. The clamp of claim 13 wherein the two arms include slots communicating with each hole suitable for slipping the pin through to the holes.

18. A method of fastening a plurality of bone fixation pins set within a plurality of bone fragments to at least one stabilization bar using a clamp with each pin, the clamp having an indentation between two arms, aligned holes in each arm for insertion of the pin through each arm and a force applicator capable of applying a force on the stabilization bar in a direction generally directed toward the pin within the holes in the arms, the method comprising the steps of:

engaging the indentation of the clamp with the stabilization bar at the desired portion on the stabilization bar, inserting the pin into the holes in the arms of the clamp; and employing the force applicator such that the stabilization bar is applying force on the pin and the pin and stabilization bar are effectively immobilized relative to the clamp.

19. The method of claim 18, further comprising the step of drilling the holes for the placement of the plurality of pins in the bone fragments using the holes in the arms of each clamp as a guide while the clamp is engaged with the stabilization bar.

20. The method of claim 18, further comprising the step of changing the configuration of the plurality of bone fixation pins without disrupting the clamping of the pins whose location on each respective clamp is not being changed.

21. The method of claim 18, wherein the clamp further comprises a retaining clasp for gripping the stabilization bar within the indentation to resist the separation of the clamp from the stabilization bar before the step of inserting the pin.

* * * * *

UNITED STATES PATENT AND TRADEMARK OFFICE
CERTIFICATE OF CORRECTION

PATENT NO. : 5,674,221
DATED : October 7, 1997
INVENTOR(S) : Todd J. Hein; Jude L. Sasing It is certified that error appears in the above-indentified patent and that said Letters Patent is hereby corrected as shown below:

On the title page, line 1 of the title, between "WITH" and "IMPROVED" insert --AN--.

Col. 1, line 1 of the title, between "WITH" and "IMPROVED" insert --AN--.

Col. 3, line 39, delete "lot" and insert therefor --slot--.

Col. 3, line 43, between "is" and "top" insert --a--.

Col. 7, line 34, delete "supports" and insert therefor --support--.

Col. 7, line 48, delete "properly" and insert therefor --property--.

Col. 8, line 21, delete "clam" and insert therefor --claim--.

Col. 8, line 53, delete "provides" and insert therefor --provide--.

Col. 9, line 20, delete "place" and insert therefor --placed--.

Col. 9, line 38, delete "describe" and insert therefor --described--.

Col. 10, line 35, delete "treaded" and insert therefor --threaded--.

Signed and Sealed this

Sixteenth Day of June, 1998

Attest:

BRUCE LEHMAN

Attesting Officer

Commissioner of Patents and Trademarks